United States Patent
Richter et al.

(10) Patent No.: US 9,492,293 B2
(45) Date of Patent: Nov. 15, 2016

(54) METHOD AND APPARATUS FOR STENTING

(75) Inventors: Yoram Richter, Ramat-Hasharon (IL); Elazer R. Edelman, Brookline, MA (US)

(73) Assignee: Medinol Ltd., Tel Aviv (IL)

( * ) Notice: Subject to any disclaimer, the term of this patent is extended or adjusted under 35 U.S.C. 154(b) by 104 days.

(21) Appl. No.: 12/541,615

(22) Filed: Aug. 14, 2009

(65) Prior Publication Data

US 2010/0042200 A1 Feb. 18, 2010

Related U.S. Application Data (63) Continuation of application No. 10/484,081, filed as application No. PCT/US02/07529 on Mar. 13, 2002.

(60) Provisional application No. 60/275,419, filed on Mar. 13, 2001.

(51) Int. Cl.
| | |
|---|---|
| *A61F 2/86* | (2013.01) |
| *A61F 2/958* | (2013.01) |
| *A61F 2/06* | (2013.01) |
| *A61M 25/10* | (2013.01) |

(52) U.S. Cl.
CPC ............. *A61F 2/86* (2013.01); *A61F 2/958* (2013.01); *A61F 2002/068* (2013.01); *A61F 2250/0039* (2013.01); *A61M 25/1002* (2013.01)

(58) Field of Classification Search
CPC ............ A61F 2/07; A61F 2250/0039; A61F 2250/0036; A61F 2230/0069; A61F 2/86; A61F 2/958; A61F 2002/068; A61M 25/1002
USPC ........................................................ 623/1.15
See application file for complete search history.

(56) References Cited

U.S. PATENT DOCUMENTS

| | | | |
|---|---|---|---|
| 4,877,030 A | 10/1989 | Beck et al. | |
| 5,158,545 A | 10/1992 | Trudell et al. | |
| 5,292,331 A | 3/1994 | Boneau | |
| 5,456,667 A | 10/1995 | Ham et al. | |
| 5,639,274 A | 6/1997 | Fischell et al. | |
| 5,645,559 A * | 7/1997 | Hachtman ............... | A61F 2/90 606/198 |
| 5,667,486 A * | 9/1997 | Mikulich et al. ........... | 604/8 |
| 5,725,547 A | 3/1998 | Chuter | |
| 5,755,769 A | 5/1998 | Richard et al. | |
| 5,827,321 A | 10/1998 | Roubin et al. | |
| 5,922,019 A | 7/1999 | Hankh et al. | |

(Continued)

FOREIGN PATENT DOCUMENTS

| | | |
|---|---|---|
| CA | 2404330 | 10/2001 |
| EP | 0 183 372 | 6/1986 |

(Continued)

OTHER PUBLICATIONS

Extended European Search Report dated Feb. 1, 2010 from co-pending EP Application No. 09004580.8-2320.

(Continued)

*Primary Examiner* — Katherine M Shi
*Assistant Examiner* — Michael Mendoza
(74) *Attorney, Agent, or Firm* — Cadwalader Wickersham & Taft LLP (57) ABSTRACT

A method and an apparatus to create a more favorable flow regime in a lumen. An artificial shape in the lumen is created to at least one of eliminate flow disturbances and enhance aspects of fluid flow through a treatment site.

15 Claims, 10 Drawing Sheets

(56) References Cited

U.S. PATENT DOCUMENTS

| | | | |
|---|---|---|---|
| 5,938,697 | A | 8/1999 | Killion et al. |
| 5,954,743 | A | 9/1999 | Jang |
| 5,961,548 | A * | 10/1999 | Shmulewitz ............... 623/1.35 |
| 6,010,530 | A | 1/2000 | Goicoechea |
| 6,120,534 | A | 9/2000 | Ruiz |
| 6,136,022 | A | 10/2000 | Nunez et al. |
| 6,159,238 | A | 12/2000 | Killion et al. |
| 6,165,195 | A * | 12/2000 | Wilson ................. A61F 2/856 606/108 |
| 6,168,610 | B1 | 1/2001 | Marin et al. |
| 6,200,335 | B1 | 3/2001 | Igaki |
| 6,245,102 | B1 | 6/2001 | Jayaraman |
| 6,264,690 | B1 | 7/2001 | Von Oepen |
| 6,364,900 | B1 | 4/2002 | Heuser |
| 6,491,711 | B1 | 12/2002 | Durcan |
| 6,527,739 | B1 | 3/2003 | Bigus et al. |
| 6,562,066 | B1 | 5/2003 | Martin |
| 6,569,193 | B1 * | 5/2003 | Cox et al. .................. 623/1.15 |
| 6,572,648 | B1 | 6/2003 | Klumb et al. |
| 6,613,079 | B1 | 9/2003 | Wolinsky et al. |
| 6,709,449 | B2 | 3/2004 | Camrud et al. |
| 6,773,454 | B2 | 8/2004 | Wholey et al. |
| 8,273,117 | B2 | 9/2012 | Palumbo et al. |
| 2001/0010013 | A1 | 7/2001 | Cox et al. |
| 2002/0058991 | A1 * | 5/2002 | Schmitt .................... 623/1.15 |
| 2002/0165599 | A1 | 11/2002 | Nasralla |
| 2003/0097168 | A1 | 5/2003 | Lau et al. |
| 2003/0114912 | A1 * | 6/2003 | Sequin et al. ............. 623/1.11 |
| 2007/0208418 | A1 * | 9/2007 | Hegg et al. ................ 623/1.35 |
| 2012/0150282 | A1 | 6/2012 | Adden et al. |
| 2013/0253301 | A1 | 9/2013 | Park |

FOREIGN PATENT DOCUMENTS

| | | |
|---|---|---|
| EP | 1254644 A1 * | 11/2002 |
| EP | 0 861 638 | 9/2005 |
| EP | 1 135 171 | 8/2008 |
| FR | 2 744 625 | 8/1997 |
| FR | 2745172 | 8/1997 |
| JP | H 7-502673 | 3/1995 |
| JP | 3009638 | 7/1995 |
| JP | 9-168597 | 6/1997 |
| JP | H09-511409 | 11/1997 |
| JP | 2720187 | 2/1998 |
| JP | H10-508234 | 8/1998 |
| JP | H11-511679 | 10/1999 |
| JP | 2000-316982 | 11/2000 |
| JP | 2001-25508 | 1/2001 |
| WO | WO 95/14442 | 6/1995 |
| WO | WO 96/14028 | 5/1996 |
| WO | WO 97/17101 | 5/1997 |
| WO | WO 97/43983 | 11/1997 |
| WO | WO 98/43695 | 10/1998 |
| WO | WO 99/44540 | 9/1999 |
| WO | WO 00/28922 | 5/2000 |
| WO | WO 00/44308 | 8/2000 |
| WO | WO 01/06954 A1 | 2/2001 |
| WO | WO 01/060284 | 8/2001 |
| WO | WO 01/72239 | 10/2001 |
| WO | WO 02/30327 | 4/2002 |
| WO | WO 02/071975 A2 | 9/2002 |
| WO | WO 02/071975 A3 | 9/2002 |

OTHER PUBLICATIONS

Office Actions and Responses to office Actions of related U.S. Appl. No. 10/484,081: Final Rejection dated Mar. 12, 2010; Response and Claim Amendments to Non-Final Rejection dated Dec. 7, 2009; and Non-Final Rejection dated Aug. 24, 2009.

Office Actions and responses of related U.S. Appl. No. 10/484,081: Amendment and Response to Final Rejection with Request for Continued Examination dated Jul. 5, 2011; Final Rejection dated Jun. 9, 2011; Examiner Interview Summary Record dated Jun. 9, 2011; and Final Rejection dated Feb. 8, 2011.

Office Actions and Responses to Office Actions of related U.S. Appl. No. 10/484,081, Amendment and Response to Non-Final Office Action dated Nov. 3, 2010.

Office Actions and Responses of related U.S. Appl. No. 10/484,081: Amendment and Response to Final Rejection filed Jan. 9, 2014 with a Request for Continued Examination; Applicant Initiated Interview Summary dated Dec. 10, 2013; Final Rejection dated Oct. 10, 2013; Amendment and Response to Non-Final Rejection filed Sep. 19, 2013; and Non Final Rejection dated Jun. 20, 2013.

Office Actions and Response of related U.S. Appl. No. 13/236,827: Non-Final Rejection dated Nov. 20, 2013; Response to Requirement for Restriction/Election filed Oct. 9, 2013; and Requirement for Restriction/Election dated Sep. 25, 2013.

Office actions and responses of related U.S. Appl. No. 10/484,081: Amendment and Response to Final Rejection with Request for Continued Examination dated Mar. 21, 2002; Interview Summary and Final Rejection dated Dec. 23, 2011; and Final Rejection dated Oct. 7, 2011.

Office actions and response of related U.S. Appl. No. 13/236,827: Non-Final Rejection dated Sep. 4, 2014.

Rieu et al., "Radial Force of Coronary Stents: A Comparative Analysis," Catheterization and Cardiovascular Interventions 46:380-391 (1999).

Office Actions and Responses of related U.S. Appl. No. 10/484,081: Non-Final Rejection dated Jan. 28, 2014.

Office Actions and Responses of related U.S. Appl. No. 13/236,827: Supplemental Response to Non-Final Rejection dated Feb. 25, 2014; and Response to Non-Final Rejection dated Feb. 19, 2014.

Office Actions and Responses to Office Actions of related U.S. Appl. No. 10/484,081: Advisory Action dated Jun. 8, 2009; Request for Continued Examination dated Jun. 5, 2009; Advisory Action dated May 1, 2009; Amendment and Response to Final Rejection, Notice of Appeal and Extension of Time dated Apr. 9, 2009; Final Rejection dated Dec. 10, 2008; Amendment and Response to Non-Final Office Action with Extension of Time dated Jul. 28, 2008; and Non-Final Rejection dated Mar. 27, 2008.

Hehrlein Christoph, Weinschenk, Ines, and Metz, Jurgen (1999) "Long Period of Balloon Inflation and the Implantation of Stents Potentiate Smooth Muscle Cell Death. Possible Role of Chronic Vascular Injury in Restenosis," Acute Cardiac Care, 2:1, 21-26.

Supplementary Partial European Search Report dated May 21, 2007 from related EP Patent No. EP 1 367 963.

Extended European Search Report dated Jul. 6, 2009 from co-pending EP Application No. 09005594.8-2320.

* cited by examiner

METHOD AND APPARATUS FOR STENTING

CROSS-REFERENCE TO RELATED APPLICATIONS

This application is a continuation of application Ser. No. 10/484,081, which is the National Stage of International Application No. PCT/US02/07529, filed Mar. 13, 2002, which claims the benefit of Provisional Application No. 60/275,419, filed Mar. 13, 2001.

FIELD OF THE INVENTION

The present invention relates generally to implantable medical devices, and more particularly, to implantable stents for maintaining the patency of a lumen.

BACKGROUND OF THE INVENTION

Many factors are known that can contribute to and/or exacerbate an occlusion of a bodily vessel or lumen. Such factors include internally induced vascular injury, such as, for example, vascular injury caused by an accumulation of plaque at the walls of the lumen, or externally induced vascular injury, such as vascular injury caused by the deployment of a stent and/or by angioplasty. When a lumen is subjected to injury, white blood cells and other substances tend to converge on the injured region of the lumen bringing about inflammatory effects at that region. These inflammatory effects tend to result in an occlusion of the lumen, that is, an undesired narrowing of the lumen or a total blockage of the lumen. In the case of an externally induced injury resulting from a deployment of a stent, the inflammatory effects sometimes tend to contribute to what is termed restenosis, or re-occlusion of the lumen.

Moreover, in the lumen, there may be areas with flow disturbances. The vasculature in the human body is a tree of diverging lumens with typical dichotomous diverging patterns. The dichotomous diverging patterns create bifurcations in the arterial system where the mother lumen diverges into two daughter lumens. In most cases one of the daughter branches is larger and is the continuation of the mother vessel and the other one is smaller and the side branch. (The venous system is basically the mirror image of these bifurcations in which the flow is from smaller lumens into larger ones, or in the direction of flow one can describe this system as converging rather than diverging.) The present invention is in part based on an observation that vascular injury may be caused by or exacerbated by among other things flow disturbances in the flow of blood at a given region of the lumen. These flow disturbances include areas of "flow separation," in which vortices are created next to the vessel wall, rendering the blood essentially stagnant at those locations. Such areas of flow separation are a particular problem in bifurcated lesions. However, even lumens with a substantially constant diameter may have areas with undesirable flow separation or other flow disturbances.

Such disturbances may work to increase the likelihood of inflammation by increasing the residence time for inflammatory cells near the walls of the lumen, and decreasing of flow forces that might otherwise push those cells downstream. That, in turn, may increase the probability that such white cells will penetrate the wall and will initiate an inflammatory effect, which can result in an undesirable narrowing of the lumen. Flow disturbance may also be an instigator in endothelial cell dysfunction (whether due to decreased fluid shear stress at the wall, imposition of bi-directional shear stress, or otherwise) which then promotes the occurrence of an inflammatory reaction. Finally, flow disturbance may cause or exacerbate vascular injury by promoting particle sedimentation and by inhibiting proper transport of waste materials from the vessel wall into the lumen. Although the precise mechanism or mechanisms by which flow disturbance accelerates the growth of vascular lesions is not completely understood, it is believed that avoiding flow disturbance will lessen the risk of vessels narrowing or re-narrowing.

Moreover, a typical angioplasty procedure causes trauma to the vessel wall. The angioplasty procedure is typically at the area of highest constriction in a vessel, i.e., at the location of a lesion. If a stent is implanted in this area, flow disturbances may be present.

Without limiting the scope of the present invention, there are at least three factors that may influence the presence of flow disturbances at areas of constriction. First, it is unlikely that the lesion formed by chance—lesions rarely do. There must be a reason why the lesion is localized at a particular place. More than likely, this place was a point of flow disturbance to begin with. At best, stents according to the prior art do not alter the geometry of a vessel but rather return it to the original geometry. Hence there is a good chance that the stented geometry includes the flow disturbance.

Thus, an angioplasty or stent procedure likely increase inflammatory effects. First, as described above, any flow disturbances may increase the residence times for inflammatory cells near the walls of the vessel even in the absence of injury, and/or adversely effect endothelial cell function. Second, the vascular injury caused by the angioplasty and/or stent deployment enhances the likelihood of inflammation, even in the absence of flow disturbance.

Furthermore, as opposed to the optimal stent deployment discussed above, stents often do not deploy optimally, thus introducing a new flow disturbance into the system. This can be because they are not adequately tapered (which is a particular problem with conventional dedicated bifurcation stents), or because they are deployed in a curving vessel and alter that curvature, or because of sub-optimal support of a tough lesion or just because of the nature of the stent design, or because most stents (and particularly those that are dedicated bifurcation stents) do not have an angle of taper.

There are known stents which are tapered. For example, U.S. Pat. No. 5,827,321 to Roubin et al. discloses a tapered stent. The stents disclosed in that patent, however, are tapered to provide an optimized fit between the original geometry and the treated section of the lumen, so as to minimize the stretch of the lumen wall when treating a tapered section of a lumen. They are therefore specifically designed not to alter the flow characteristics of a lumen. Rather, they are specifically designed to conform to the existing geometry of the lumen.

In view of this there is a need to minimize flow disturbance and the concomitant probability of inflammatory cell adhesion/infiltration where adhesion/infiltration is deemed to be a problem. In particular there is a need to provide a method an apparatus for reshaping a lumen to promote laminar flow and minimize or eliminate any areas of flow separation, especially in areas that were traumatized by the angioplasty procedure, in order to minimize the effect of the trauma. This includes assuring the proper shaping of the lumen when stenting a bifurcation or even to creating an artificial geometry in a straight vessel where such shape was non-existing prior to the treatment, in order to minimize flow separation, that may happen if there is no shaping. Preferably, this can be done by physicians using existing devices that were not originally made to create an artificial geometry

SUMMARY OF THE INVENTION

Accordingly, the present invention provides stent configurations that induce a more favorable flow regime (e.g., one that minimizes or eliminates flow disturbance in the treatment area) are provided. Specifically, a method and apparatus is disclosed which enables a physician to tailor the flow characteristics of the post-treatment site to avoid flow disturbances, or otherwise enhance aspects of fluid flow through the post-treatment site to avoid inflammatory effects.

Embodiments of the present invention utilize a shaped, e.g., tapered, stent such that the flow pattern, as it relates to the probability of restenosis, is optimized relative to that which would be induced by a stent that was either non-tapered or tapered in such a way as to merely minimize the mechanical stress imposed on the wall.

The aspects of the flow pattern that may be optimized by the appropriate tapered geometry may include any one (or a combination) of the following:

a. Reduction/elimination of regions of flow separation. Such regions are most commonly found in bifurcated geometries.

b. Increase in the shear stress imposed on the vessel wall by fluid flow.

c. Introduction/enhancement of acceleration of mean fluid velocity along the length of the stent.

d. Reduction/elimination of the radial (perpendicular to the vessel wall) component of fluid flow.

e. Replacement of bi-directional (forward and backward) shear stress with a unidirectional shear stress.

f. Promotion of mass transport out of the vessel wall.

g. Transition of potentially non-laminar flow pattern to laminar flow.

h. Other, as yet undescribed, aspects. The study of what exactly is it about flow disturbance that enhances restenosis is ongoing. The inventors do not know everything about how this happens but have discovered that improving the flow regime minimizes the probability of re-occlusion.

The optimization obtainable with embodiments of the present invention can be achieved in vessel geometries that either:

1. Include a region of flow disturbance (most commonly flow separation); the most common examples of this would be bifurcations. This region of flow disturbance which exists after stenting with present devices predisposes the stent to re-occlusion for any one of the factors mentioned above. Hence, reduction/elimination of the region of disturbance minimizes the probability of re-occlusion.

2. May not include a region of flow disturbance; the most common examples of this would be straight, tapered/non-tapered, non-bifurcated vessel segments. The stent is still predisposed to re-occlusion (as all stents are) due to a multitude of factors including vessel wall injury, inflammatory response, foreign body reaction etc, but the introduction of an artificial geometry in these cases alters the flow pattern in such a way as to offset non flow-disturbance related factors with the end result being a minimization of the probability of restenosis.

Embodiments of stents with axially symmetric or asymmetric tapers are disclosed. An axially asymmetric taper may be deployed in geometries that include a region of flow disturbance (most commonly flow separation; see 1 above). The stent would be deployed such that the tapered part of its circumference would face the region of flow disturbance. An axially symmetric taper would typically be deployed in geometries that may not include a region of flow disturbance (see 2 above). However, for considerations of manufacturability, usability, marketing or otherwise, an axially symmetric taper could still be used even in geometries that do include regions of flow separation (see 1 above) with results that would be expected to be superior to those that would be achieved with a non-tapered stent.

The shape of the stent may be specifically designed to improve the flow regime, e.g., by minimizing any flow disturbance, and the resultant narrowing of the lumen. This may be accomplished with a self-expanding stent that has, for example, at least two sections with different cross-sectional areas, and a tapered section connecting the two sections with different cross-sectional areas to one another. Of course these sections will have different cross-sectional areas.

In another embodiment, a balloon expandable stent may be implanted with a delivery balloon which is shaped to cause it to deploy to a predetermined shape. The shaped portion of the stent may be positioned at the bifurcation or at the sensitive area (e.g., a lesion site) in a straight vessel. This permits physicians to use existing stents that were not originally designed to have a non-uniform shape to carry out the present invention and create a shaped, e.g., tapered geometry in a lumen. Of course, the stent may be shaped and expanded to its predetermined shape by a balloon or balloons of appropriate compliance to form the desired shape.

Thus, in a straight lumen, the stent may be configured to introduce an artificial tapering. In some cases, for example at a bifurcation, that tailoring may be accomplished by using a stent with an axially asymmetric profile in the expanded shape. In other cases, for example a vessel whose pre-diseased shape was generally straight and of generally constant diameter, that tailoring may be accomplished by inducing an artificially tapered section or sections.

Thus, these embodiments provide a method and apparatus for reshaping a lumen to promote more favorable flow regime, e.g., laminar flow, and minimize or eliminate any areas of flow separation, especially in areas that were traumatized by the angioplasty procedure in order to prevent restenosis. In general terms, this is done using stents that are configured to minimize flow disturbance. In the illustrated embodiments, these stents are configured so that they have a taper which alters the flow characteristics of the lumen.

BRIEF DESCRIPTION OF THE DRAWINGS

The present invention is illustrated by way of example and not limitation in the figures in the accompanying drawings in which like references indicate similar elements, and in which:

FIG. 4b is a side elevational wire frame view of the profile of the stent of FIG. 4a;

FIG. 5b is a side elevational wire frame view of the stent of FIG. 5a;

FIG. 6b is a side elevational wire frame view of the stent profile of FIG. 6a;

DETAILED DESCRIPTION

The present invention is in part based on an observation that vascular injury may be caused by or exacerbated by, among other things, flow disturbances in the flow of blood at a given region of the lumen. Flow disturbances in the form of flow separation might work to increase the likelihood of inflammation by increasing a residence time for inflammatory cells near the walls of the lumen, by decreasing fluid shear stress at the wall, by imposing bi-directional shear stress, by promoting particle sedimentation and by decreasing mass transfer of waste products from the wall into the lumen. Flow separation is manifested in regions where flow vortices are created next to lumen walls, or where blood is substantially stagnant next to the lumen walls. Flow disturbances also may tend to adversely affect endothelial cell function and hence prevent the endothelial cells from providing a barrier to inflammatory cell infiltration. Although the precise mechanism or mechanisms by which flow disturbance accelerates the growth of vascular lesions is not completely understood, it is believed that avoiding flow disturbance will lessen the risk of vessels narrowing or re-narrowing.

In most general terms, embodiments of the present invention are directed to disposing a stent, specifically designed to induce a more favorable flow regime, in an area where an undesirable flow disturbance would otherwise occur. This is done using a stent, which, when expanded will have a non-uniform shape. In other words, its shape deviates from the conventional longitudinally uniform circular cross-section found in most stents.

In the following, exemplary shapes will be described. These are only given as examples. Other shapes which, based on the principles of fluid dynamics, will, in a particular instance, avoid flow disturbances may be also used. Also described are the various types of stents that may be used, such as self-expanding stents and balloon-expandable stents along with ways of achieving the desired stent profiles of shapes and delivering the stents.

Exemplary Shapes

FIGS. 2a-7b and 10 illustrate profiles of expanded stents according to the present invention. It is noted that although FIGS. 2a-7b and 10 are sometimes referred to as showing a "stent," what these figures actually show is a schematic view of the stent envelope or profile, without showing cell patterns or other stent configurations that would in turn contribute to form the shown stent envelopes.

In general, the stent profiles illustrated in FIGS. 2a-7b and 10 can be considered to comprise a first stent segment 12 configured to have at least a first stent cross-sectional area A1 in the expanded state of the stent as shown. A second stent segment 14 is longitudinally offset with respect to the first stent segment 12 and is configured to have a second stent cross-sectional area A2 in the expanded state of the stent as shown. The stent also includes a third stent segment 16 configured to assume a tapered stent segment configuration in the expanded state of the stent as shown, the tapered stent segment configuration connecting the first stent segment 12 to the second stent segment 14.

The stent may be configured such that, in an expanded state thereof in a lumen, it manipulates a flow of blood in the lumen so as to reduce or eliminate flow disturbances at the treatment site after the stent is placed. In each of the illustrated embodiments, the cross-sectional area of the stent varies as will be apparent from the description that follows.

In the context of the present invention, a "stent segment" refers to any portion of the stent envelope defined between two boundary regions, such as boundary planes perpendicular to the longitudinal axis of the stent. In particular, in embodiments of the present invention, the first stent segment 12 is a stent segment having a constant stent cross-sectional area A1 in a deployed state of the stent, this first stent segment 12 being defined between planes P1' and P1", where P1' is a plane located at the inlet opening I of the stent. The second stent segment 14 in turn has a constant stent cross-sectional area A2 in a deployed state of the stent, this second stent segment 14 being defined between planes P2' and P2", where P2" is a plane located at the outlet opening O of the stent. The third stent segment 16 is has a tapered configuration in a deployed state defined between planes P3' and P3" and is tapered in a expanded state of the stent. According to embodiments of the present invention, the tapering of third stent segment may be either continuous, as shown in the embodiments of FIGS. 2a-7b and 10, or stepped (not shown). Referring in particular to embodiments of the present invention shown in FIGS. 2b, 3b, 4b, 5b, 6b, 7a, 7b and 10, planes P1', P1", P2', P2", P3', and P3" are shown for respective ones of those embodiments.

Figure 2A:
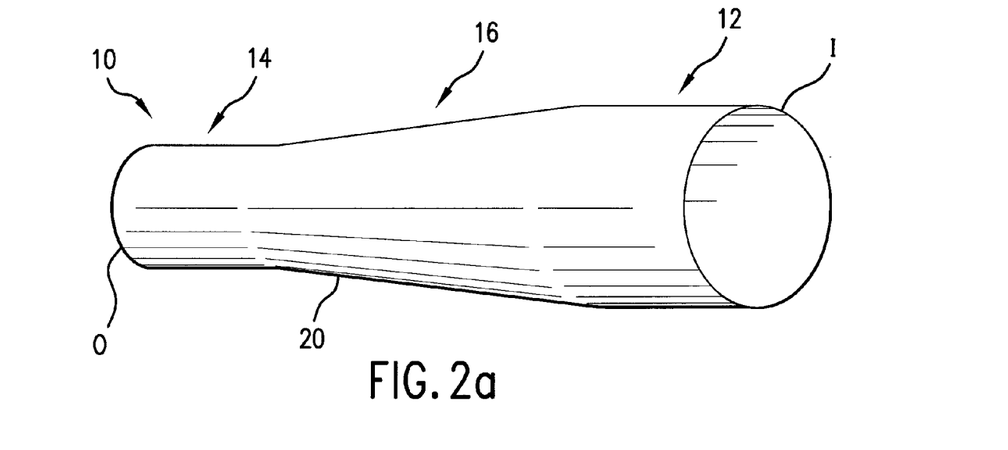
FIG. 2a is a perspective, schematic view of a profile of an expanded stent according to a first embodiment of the present invention.
Figure 2B:
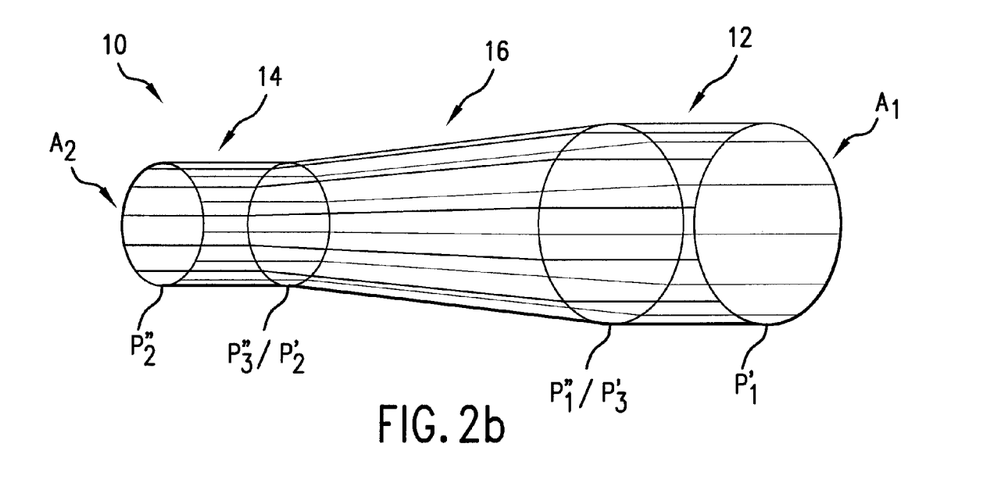
FIG. 2b is a view similar to FIG. 2a showing the profile of the stent in a perspective wire frame view.
Figure 2C:
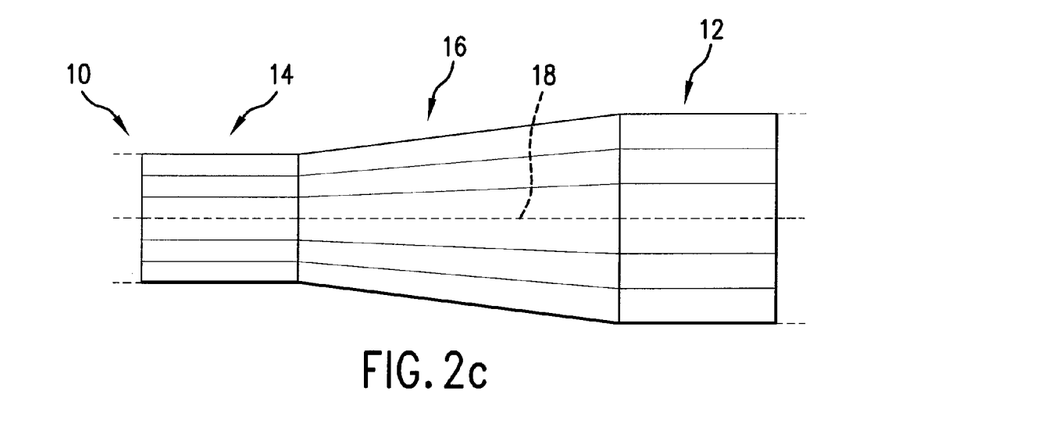
FIG. 2c is a side elevational wire frame view of the stent profile of FIGS. 2a and 2b.

FIGS. 2a-2c show a stent profile 10 comprising a first straight segment followed by a tapering segment leading to a final straight segment. In the embodiment of FIGS. 2a-2c, the first stent segment 12 is defined between planes P1' and P1", where the latter two planes are longitudinally offset with respect to one another, defining a first stent segment 12 that is a right circular cylinder therebetween. The second stent segment 14 is defined between planes P2' and P2", these two planes also being longitudinally offset with respect to each other, defining a second stent segment 14 that is also a right circular cylinder. In the embodiment of FIGS. 2a-2c, the respective ends of first, second and third stent segments are congruent, that is, P1" is coextensive with P3', and P3" is coextensive with P2' as clearly shown in FIG. 2b. In the context of the present invention, when given boundary planes of two stent segments are coextensive, it is said that those two stent segments are "directly" connected to one another. The embodiment of stent profile 10 shown in FIGS. 2a-2c may be used in a lumen having a non-tapered original shape, and in this case would change the shape of that lumen to an artificial, tapered shape.

The embodiment of stent 10 shown in FIGS. 2a-2c may also be used in a lumen that had a natural taper in an original shape thereof, in which case the first stent segment 12 may have a cross-sectional area A1 corresponding to the original shape of a proximal part of the lumen, the second stent segment 14 may have a cross-sectional area A2 corresponding to the original shape of a distal part of the lumen, and the third stent segment 16 has a tapered configuration designed to minimize or eliminate flow separation in that segment.

Figure 3A:
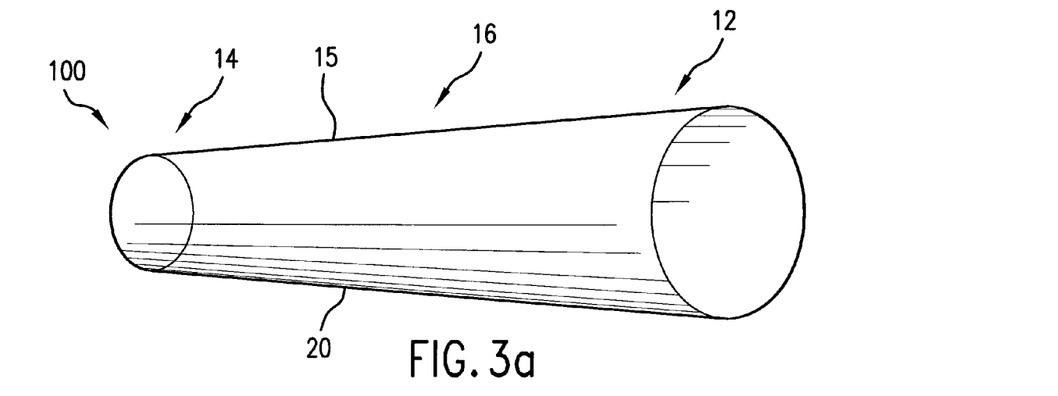
FIG. 3a is a perspective, schematic view of a profile of an expanded stent according to a second embodiment of the present invention.
Figure 3B:
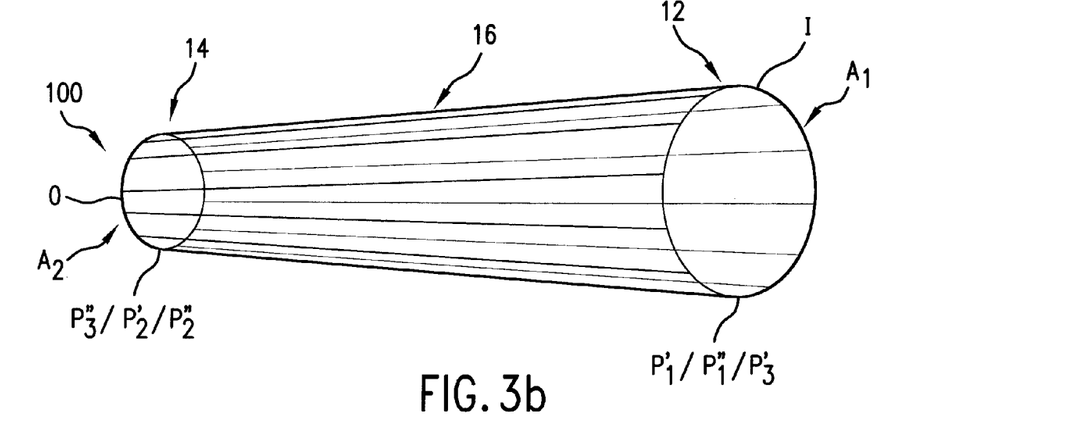
FIG. 3b is a view similar to FIG. 3a showing the profile of the stent in a perspective wire frame view.
Figure 3C:
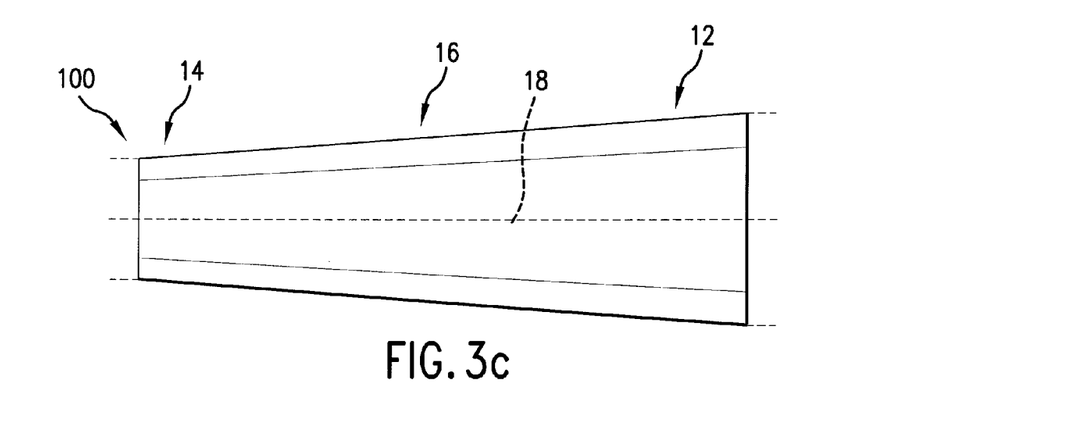
FIG. 3c is a side elevational wire frame view of the profile of stent of FIGS. 3a and 3b.

FIGS. 3a-3c show a stent profile 100 comprising one long tapered segment 5. In the embodiment of FIGS. 3a-3c, boundary planes P1' and P1" are coextensive, meaning that the first stent segment 12 is defined at the plane of the inlet I of stent 100. Similarly, boundary planes P2' and P2" are coextensive, meaning that the second stent segment 14 is defined at the plane of the outlet O of stent 100. Additionally, P3' is coextensive with both P1' and P1", meaning that the third stent segment 16 is directly connected to the first stent segment 12, and P3" is coextensive with both P2' and P2", meaning that the third segment 16 is likewise directly connected to the second stent segment 14. A configuration such as the one described above results in a stent 100 having a stent envelope 20 that defines a frustoconical shape, that is, a constant, symmetrical taper along the longitudinal axis 18 of the stent. The embodiment of FIGS. 3a-3c may be used similarly to the embodiment of FIGS. 2a-2c.

Embodiments of the stent profiles according to the present invention include within their scope stent configurations where the stent envelope presents any number of diverging segments between boundary planes P1" and P3', and between boundary planes P3" and P2'. Examples of such diverging segments are provided in the embodiments 4a-7b. Other such diverging segments may be tailored to produce the desired flow characteristics, and are within the purview of the present invention.

Figure 4A:
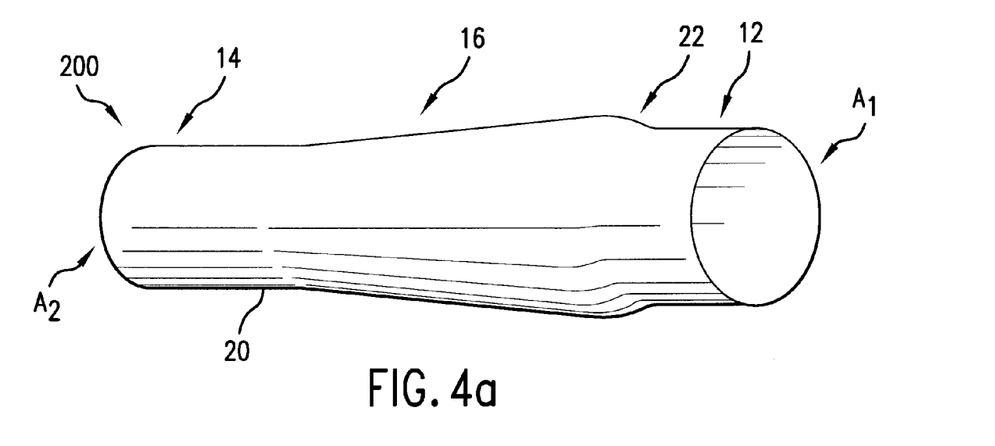
FIG. 4a is a perspective, schematic view of a profile of an expanded stent according to a third embodiment of the present invention.
Figure 4B:
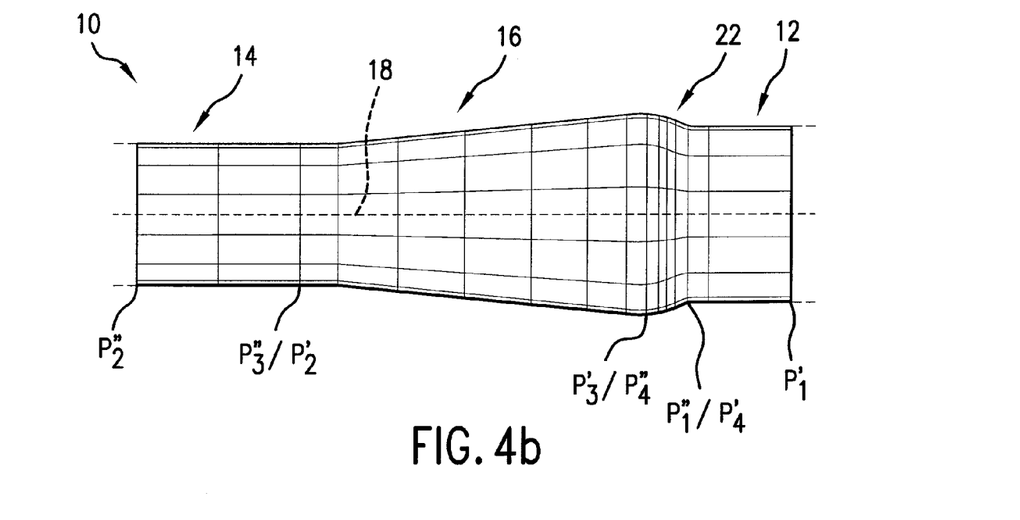

In particular, the stent profile 200 of the embodiment of FIGS. 4a-4b is similar to that of FIGS. 2a-2c, except that it further includes a fourth stent segment 22 having a diverging configuration in an expanded state of the stent, the fourth stent segment 22 being defined between boundary planes P4' and P4" as shown. In the shown embodiment, P4' is coextensive with P1", and P4" is coextensive with P3', meaning that the fourth stent segment 22 is directly connected to both the first stent segment 12 and the third stent segment 16. Here, the fourth stent segment 22 represents a diverging entrance segment.

Figure 5A:
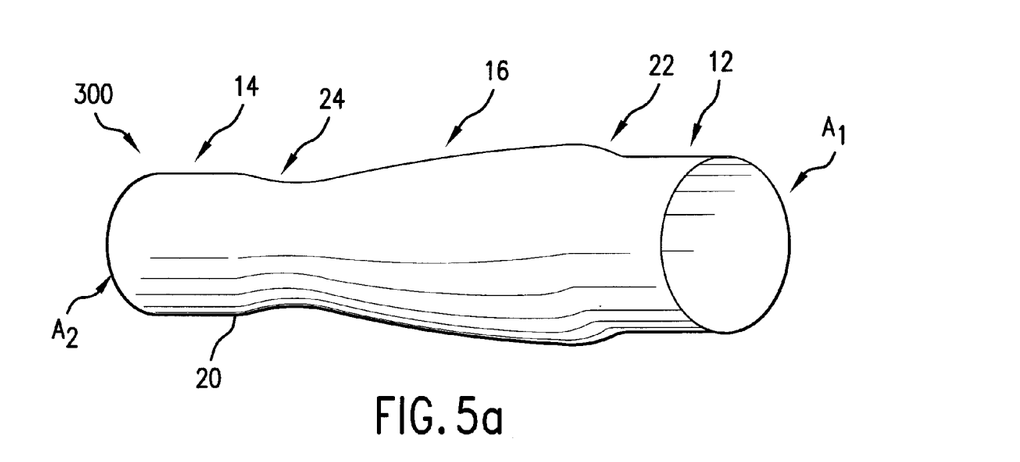
FIG. 5a is a perspective, schematic view of a profile of an expanded stent according to a fourth embodiment of the present invention.
Figure 5B:
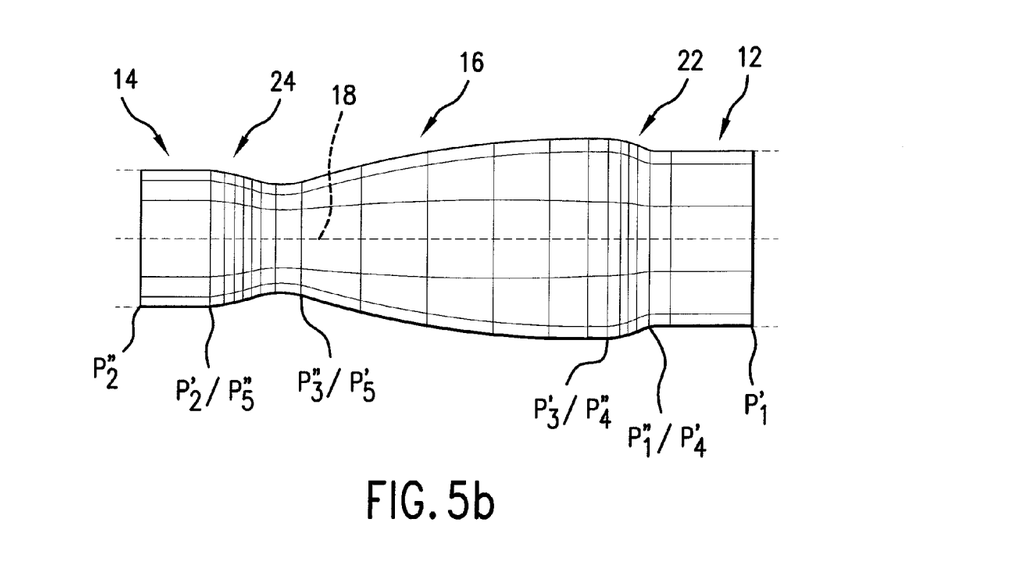

Additionally, the stent profile 300 of the embodiment of FIGS. 5a-5b is similar to the embodiment of FIGS. 4a-4b in that it additionally includes a fifth stent segment 24 having a diverging configuration with respect to an expanded state of the stent, the fifth stent segment 24 being defined between boundary planes P5' and P5" as shown. In the shown embodiment, P5' is coextensive with P3", and P5" is coextensive with P2', meaning that the fifth stent segment 24 is directly connected to both the third stent segment 16 and the second stent segment 14. Here, the fifth stent segment 24 represents a diverging exit segment.

Figure 7A:
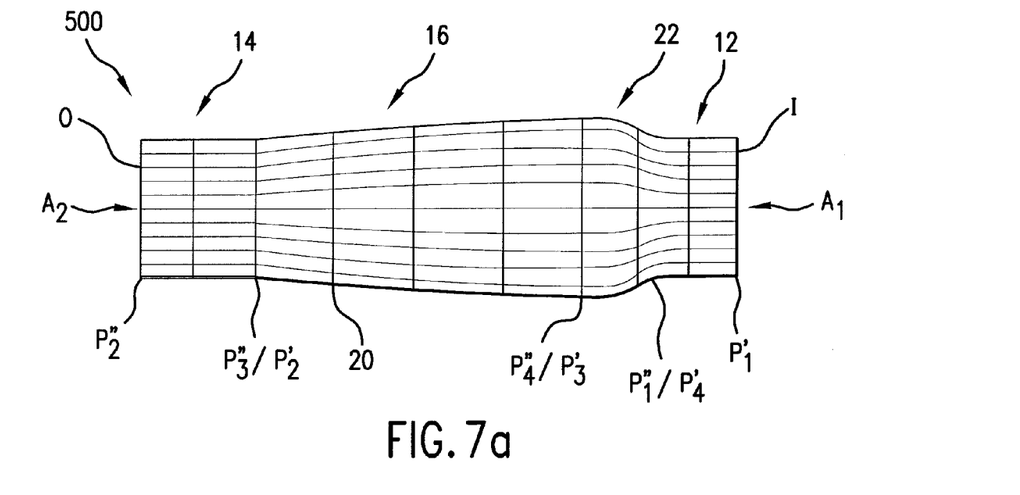
FIG. 7a is a side elevational wire frame view of a profile of an expanded stent according to a sixth embodiment of the present invention.
Figure 7B:
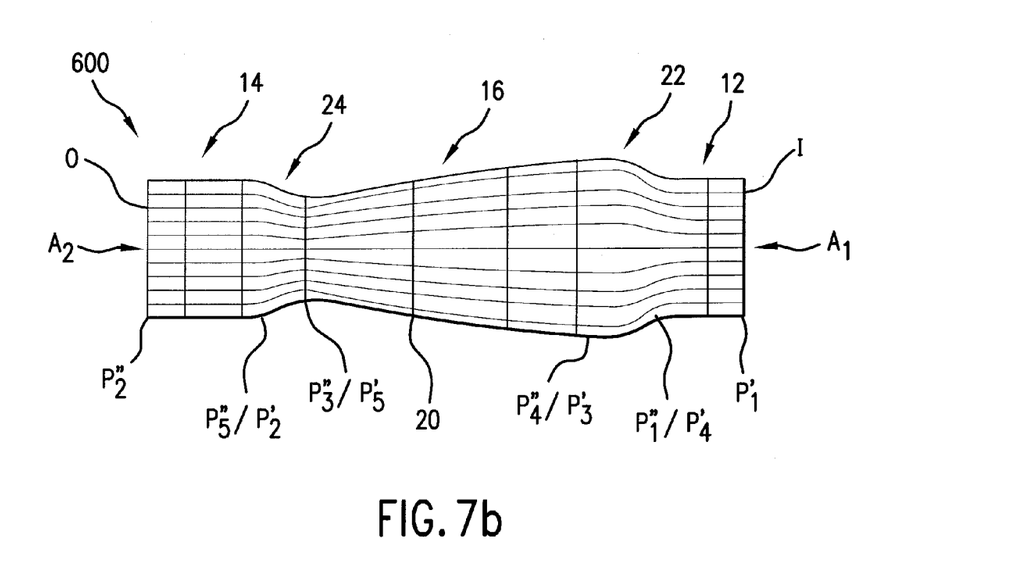
FIG. 7b is a side elevational wire frame view of a profile of an expanded stent according to a seventh embodiment of the present invention.

FIGS. 7a and 7b show two embodiments of stent profiles 500 and 600 according to the present invention, where the inlet cross-sectional area A1 is the same as outlet cross-sectional area A2. Stent profile 500 of FIG. 7a is similar to stent profile 200 of FIG. 4b, except that in the embodiment of FIG. 4b, A2 is less than A1. Moreover, stent profile 600 of FIG. 7b is similar to stent profile 300 of FIG. 5b, except that in the embodiment of FIG. 5b, A2 is likewise less than A1.

The embodiments of the stent that include one or more diverging segments between first stent segment 12 and the second stent segment 14 are useful in allowing the selection of tapering angle despite the inlet cross-sectional area, or cross-sectional area A1 of the first stent segment 12, or the outlet cross-sectional area, or cross-sectional area A2 of the second stent segment 14. One or more diverging segments can increase a cross-sectional area of the stent at boundary plane P3' with respect to cross-sectional area A1, and/or decrease a cross-sectional area of the stent at boundary plane P3" with respect to outlet cross-sectional area A2, in this way allowing an advantageous manipulation of the tapering angle in order to obtain the desired flow characteristics without being limited by inlet cross-sectional area A1 or outlet cross-sectional area A2, whether A2 is less than A1, as in the case of the embodiments shown in FIGS. 2a-5b and 10, or whether A2 is the same as A1, as in the case of the embodiments shown in FIGS. 7a-7b.

Embodiments where two diverging segments 22 and 24 are used in the stent of the present invention and where A1 and A2 are substantially equal to one another, such as the embodiment shown in FIGS. 7a-7b described above, are advantageous in that they allow a taper in the stent while allowing the inlet cross-sectional area A1 and outlet cross-sectional area A2 to be identical. Again, however, there is a variation in cross-sectional area along the length of the stent.

Asymmetrical stent configurations are possible in accordance with the principles of the present invention. For example, it is possible to provide stents that are non-uniform about the axis of the stent. This non-uniformity refers to the stent envelope, and not necessarily to the actual cells of a stent (although modifying the cells is one way to modify the stent envelope). Thus, in the embodiment of FIGS. 6a-6b on the one hand, and of FIG. 10 on the other hand, two respective examples of an asymmetrical stent profile according to the present invention are provided, that is, examples of a stent that is asymmetrical with respect to the longitudinal axis 18 thereof.

Figure 6A:
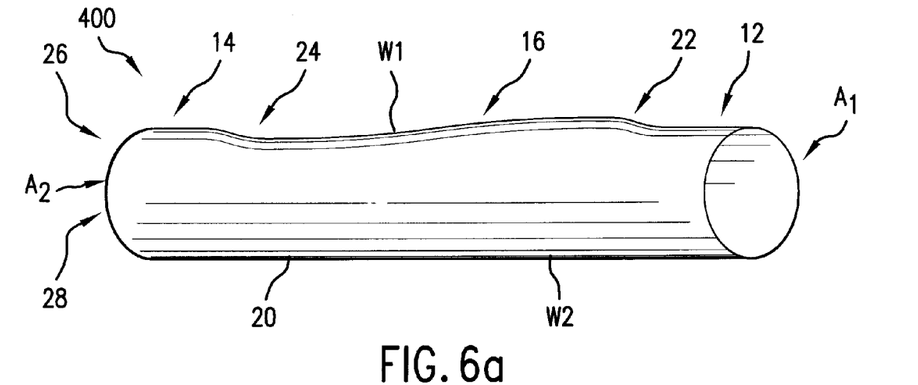
FIG. 6a is a perspective, schematic view of a profile of an expanded stent according to a fifth embodiment of the present invention.
Figure 6B:
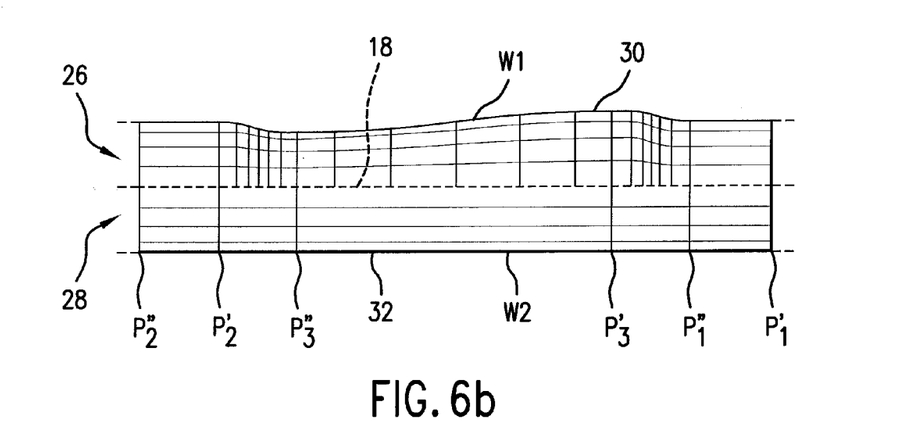

In the shown embodiments of FIGS. 6a-6b, stent profile or stent 400 has a stent envelope 20 that is configured such that, in an expanded state of the stent 400, it defines a first portion 26 bounded by walls W1 and having a contour in a cross-sectional plane including the longitudinal axis of the stent that is a curved line. A contour of first portion 26 in the cross-sectional plane including the longitudinal axis of the stent is provided for example in FIG. 6b, where the contour of wall W1 in that cross-sectional plane is curved line 30.

The stent envelope 20 in the embodiment of FIGS. 6a-6b further includes a second portion 28 bounded by walls W2 and having a contour in a cross-sectional plane including the longitudinal axis of the stent that is a straight line parallel to the longitudinal axis. This latter contour 32 is also shown in FIG. 6b. The first portion and the second portion together define the stent envelope 20 as shown. In the embodiment of FIGS. 6a and 6b, the second portion is quonset-shaped, that is, has the shape of a right cylinder cut in half along a plane that contains its longitudinal axis.

Figure 10:
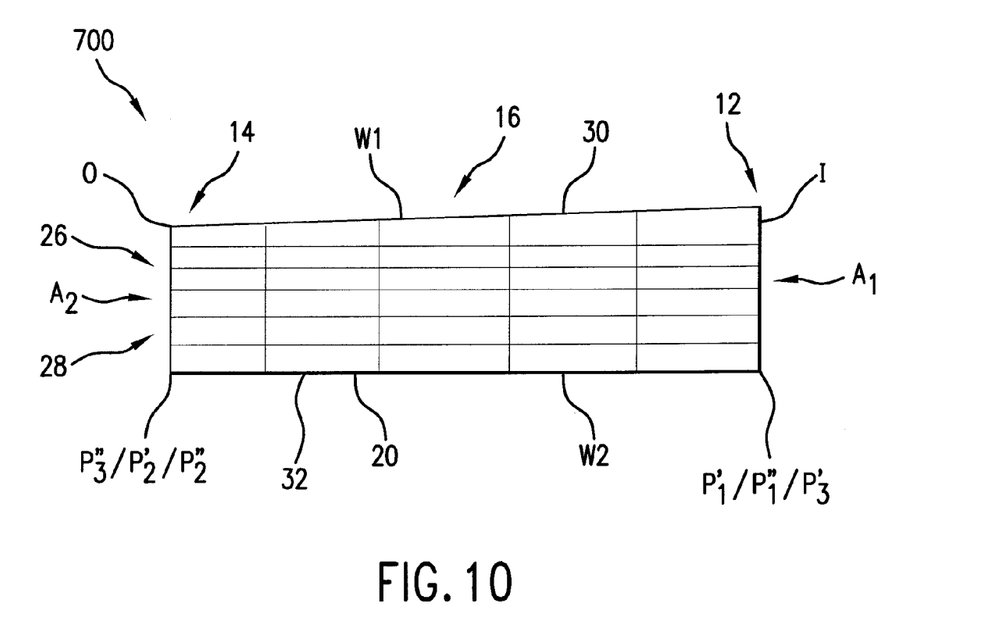
FIG. 10 is a side elevational wire frame view of a profile of an expanded stent according to an eighth embodiment of the present invention.

Moreover, in the embodiment of FIG. 10, an example of an asymmetrical stent profile or stent 700 is provided. In the shown embodiment, the stent envelope 20 is configured such that, in an expanded state of the stent 700, it defines a first portion 26 bounded by walls W1 and having a contour 30 in a cross-sectional plane including a longitudinal axis of the stent that is a straight line extending at an angle with respect to the longitudinal axis. The stent envelope 20 in the embodiment of FIG. 10 further includes a second portion 28 bounded by walls W2, and having a contour 32 in a cross-sectional plane including the longitudinal axis of the stent that is a straight line parallel to the longitudinal axis. The first portion and the second portion together define the stent envelope 20 as shown. In the embodiment of FIG. 10, the second portion 28 is quonset-shaped. The embodiment of FIG. 10 is a preferred embodiment of a stent profile according to the present invention. It is to be understood, however, that asymmetrical stents different from the one shown in the embodiments of FIGS. 6a-6b and 10 are within the purview of the present invention, as long as they are configured to induce a favorable flow regime for reducing a risk of restenosis.

The embodiments of the stent of the present invention shown in FIGS. 2a-5b, 7a and 7b, are predominantly configured to change a shape of the lumen to an artificial, tapered shape. On the other hand, asymmetrical embodiments of the stent of the present invention, that is, embodiments of stent that are asymmetrical with respect to the longitudinal axis of the stent, such as the embodiments of FIGS. 6a-6b and 10, are predominantly configured to be used at a main branch of a bifurcation, either restoring the shape of the main branch to its original shape, or changing the shape of the main branch to an artificial, tapered shape.

The stent 500 and 600 of FIGS. 7a-7b may be used according to embodiments of the present invention in a main branch of a bifurcation. In the embodiments of FIGS. 7a-7b, A1 and A2 may correspond to the actual cross-sectional area of the lumen, and, despite A1 and A2, the shape of the lumen is changed to an artificial tapered shape by virtue of the third stent segment 16, and the fourth and fifth diverging segments 22 and 24.

Stents according to embodiments of the present invention, such as the embodiments depicted in FIGS. 2a-7b and 10, may have, in an undeployed state thereof, a tapered shape that mimics the respective tapered shapes of the embodiments of FIGS. 2a-7b and 10, or a non-tapered shape that is configured to assume a tapered shape in a deployed state thereof according to embodiments of the present invention as explained in more detail below.

According to the present invention, for example, one may configure embodiments of the stent of the present invention for a straight, either tapered or non-tapered, non-bifurcated lumen. Although a non-tapered stent used at such a deployment location would still be predisposed to restenosis due to a multitude of factors, including lumen wall injury, inflammatory response, foreign body reaction, providing the lumen instead with an artificial, tapered shape according to embodiments of the present invention would manipulate the flow regime in such a way as to at least partially offset non-flow-disturbance related factors, an end result being a reduction in the risk of restenosis.

The taper in the stent according to embodiments of the present invention could be either symmetrical with respect to the longitudinal axis 18 of the stent, such as, for example, shown by way of example in the embodiments of FIGS. 2b-5b, 7a and 7b, or asymmetrical with respect to the longitudinal axis of the stent, as shown by way of example in the embodiments of FIGS. 6a-6b and 10. It is noted that the present invention includes within its scope symmetrical and asymmetrical tapered stents having configurations other than those shown by way of example with respect to the embodiments of FIGS. 2a-7b and 10, as long as the configuration of the stent manipulates a flow regime at the deployment location thereof to reduce a risk of restenosis at the deployment location.

In general, but without limitation, an axially symmetric taper, such as the one shown by way of example in the embodiments of FIGS. 2a-5b, 7a and 7b, might be preferably deployed according to embodiments of the present invention, in a vessel that is generally straight, and not bifurcated. An axially asymmetric taper, such as the one shown by way of example in the embodiments of FIGS. 6a-6b and 10 might be deployed at a bifurcation site, where the side branch is situated opposite the asymmetry, e.g., approximately at W2 in FIGS. 6a and 10.

Where the stent is configured to change a shape of the lumen to an artificial shape, and, additionally, where the stent is used in a lumen where flow separation either caused or exacerbated vascular injury, the artificial shape, and hence the outer shape of the stent envelope 20, are configured for substantially eliminating such flow separation in the lumen at the deployment location of the stent, thereby reducing a risk of restenosis at the deployment location.

The Construction and Delivery of the Stents

In one embodiment of the stent, the stent is a self-expanding stent. In one exemplary embodiment of the self-expanding stent, the self-expanding stent has at least two sections with different cross-sectional areas, and a tapered section connecting the two sections with different cross sectional areas to one another such as is shown in FIG. 2a-2c. The configurations of the other embodiments described in FIGS. 3a-7b and 10 may also be implemented as self-expanding stents.

The stent of the present invention may also be balloon-expandable stent. A balloon-expandable stent in accordance with the present invention is configured to introduce an artificial taper to a lumen. The stent may be constructed so that when expanded by a compliant balloon, for example, it will take a predetermined shape, such as one of the shapes illustrated in FIGS. 2a-7b and 10.

In another embodiment of the present invention, as described in detail below, a balloon-expandable stent is implanted with a delivery balloon, which is tapered. Deploying a balloon-expandable stent with a tapered delivery balloon will cause the stent to deploy to the tapered shape of the balloon.

Figure 8:
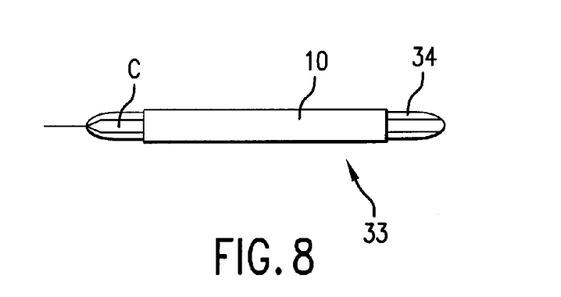
FIG. 8 is a perspective view of an embodiment of a kit according to the present invention showing a stent according to the present invention disposed over a balloon on a catheter for insertion into a lumen.
Figure 9A:
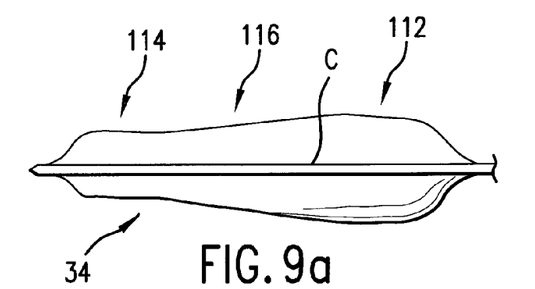
FIGS. 9a-9h are side-elevational views of deployment balloons adapted to expand a balloon-expandable stent to the configurations of FIGS. 2a, 3a, 4a, 5a, 6a, 7a, 7b, and 10, respectively.
Figure 9B:
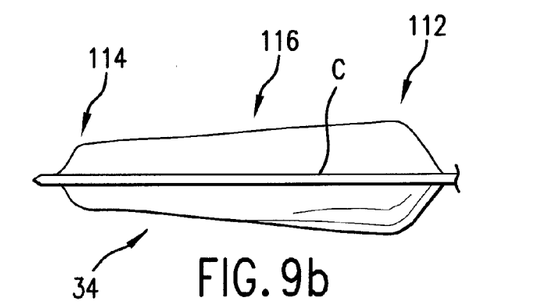
Figure 9C:
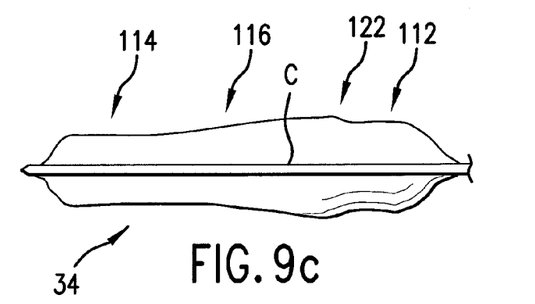
Figure 9D:
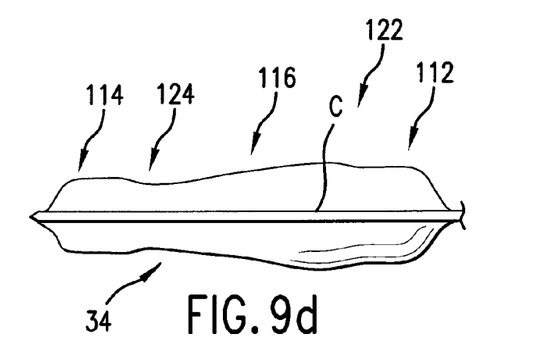
Figure 9E:
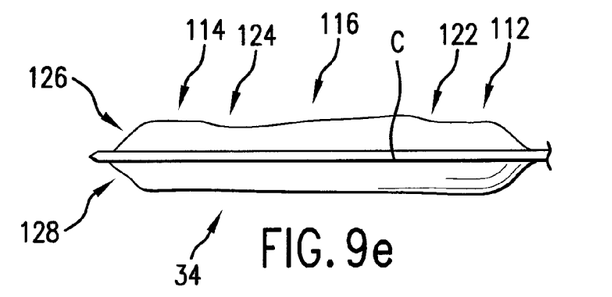
Figure 9F:
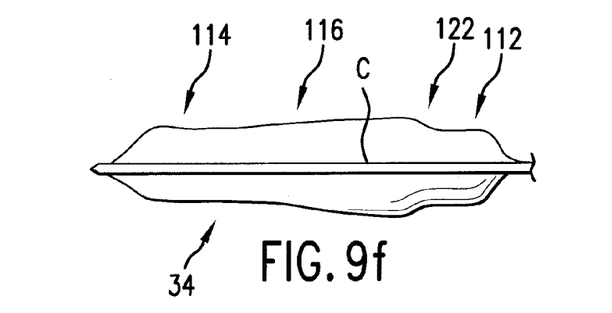
Figure 9G:
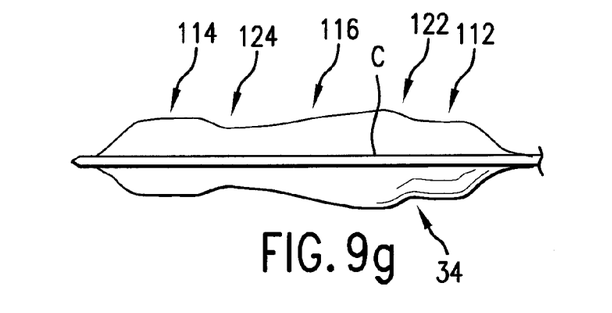
Figure 9H:
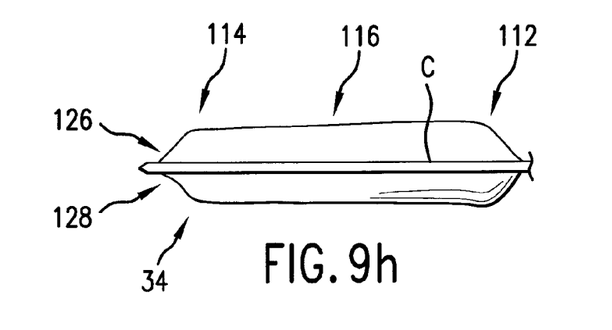

The present invention further contemplates a kit for deploying the stent 1 of the present invention. As depicted in FIG. 8, the kit includes a stent according to any one of the embodiments of the present invention, such as the embodiments described above, and a delivery balloon 34, for example on a catheter C, configured to be inflated for expanding the stent in a lumen such that, in an expanded state of the stent, the stent has any one of the configurations according to the present invention, such as those described above with respect to FIGS. 2a-7b and 10.

In this connection, the tapered shape of the stent may be produced by utilizing a balloon that has the desired profile when expanded, or it may be produced by using a compliant or semi-compliant balloon of regular profile along with a stent whose wall design is preferentially expandable at some locations, in order to produce the desired post-expansion shape.

In general terms, a balloon expandable stent and balloon are together configured to produce a tapered shape after deployment. The tapered portion or portions of the stent will be configured so as to minimize or eliminate flow disturbances throughout the treatment site. That may be accomplished with a tapered balloon forming a conventional stent, or with compliant balloon(s), semi-compliant balloon(s), or some combination of compliant, semi-compliant, and/or non-compliant balloon(s), which would permit physicians to use existing stents to carry out the present invention and create a tapered geometry in a lumen. Alternatively, it may be accomplished by configuring the stent and balloon combination to produce the desired tapering geometry on deployment.

Various embodiments of possible shaped balloons 34 according to the present invention are depicted in FIGS. 9a-9h, those figures corresponding, respectively, to balloons preferably adapted to be used in balloon expandable versions of the stent embodiments of FIGS. 2a-7b and 10.

Thus, with respect to shaped balloons, as shown by way of examples in the embodiments of FIGS. 9a-9h, the balloon 34 on catheter C includes a first balloon segment 112 configured to have a first balloon segment cross sectional area in an inflated state of the balloon for expanding the first stent segment 12 to the first stent cross-sectional area A1. A second balloon segment 114 is longitudinally offset with respect to the first balloon segment 112 and is configured to have a second balloon segment cross-sectional area in an inflated state of the balloon for expanding the second stent segment 14 to the second stent cross-sectional area A2, the second balloon segment diameter being either different from the first balloon segment diameter, as in FIGS. 9a-9e and 9h, or substantially equal to the first balloon segment diameter, as in FIGS. 9f-9g. A third balloon segment 116 is configured to assume a tapered balloon segment configuration in an inflated state of the balloon, the tapered balloon segment configuration connecting the first balloon segment 112 to the second balloon segment 114.

The balloon 34 is configured such that, in an inflated state thereof in a lumen, it expands the stent into an expanded shape that minimizes or eliminates flow disturbances at the treatment site. Optionally, balloon 34 may have one or more diverging segments 122, 124 as shown in FIGS. 9c-9g. Optionally, balloon 34 is asymmetrical with respect to a longitudinal axis thereof, as shown by way of example in FIGS. 9e and 9h, and includes a first portion 126 that is tapered, and a second portion 128 that presents a straight longitudinal contour. In such axially asymmetric embodiments, a delivery system which provides the operator with control over the rotational position of the stent about the longitudinal axis may be used.

In another embodiment, a self-expandable stent may be delivered in a conventional manner, and then reconfigured after delivery with a tapered balloon to introduce an artificial taper in the stent.

Thus, the present invention further provides a method of deploying a stent comprising: delivering the stent to a deployment location in a lumen; expanding the stent such that, in an expanded state thereof, the stent is expanded into an expanded shape which minimizes or eliminates flow disturbances at the treatment site.

Figure 1A:
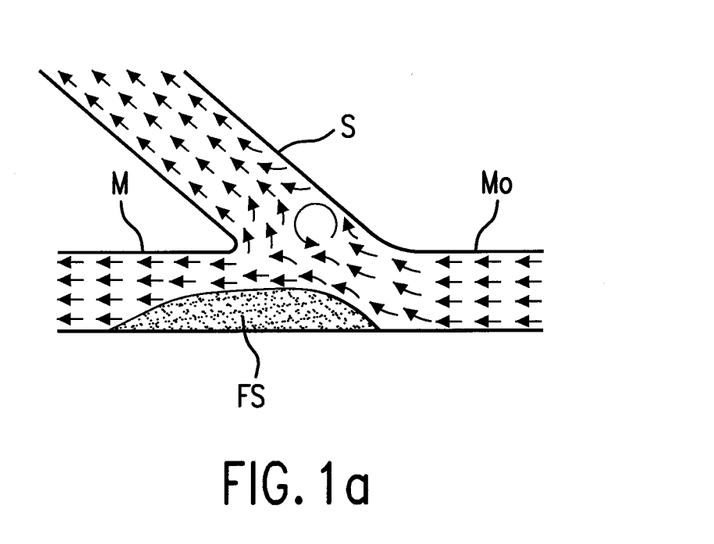
FIG. 1a is a particle image velocimetry representation of an untapered bifurcation site in a lumen, showing the flow vector field by way of arrows, and a highlighted region of flow separation.
Figure 1B:
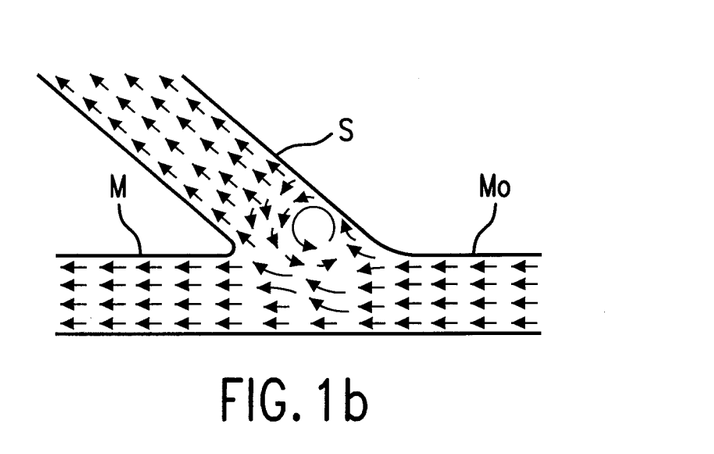
FIG. 1b is a particle image velocimetry representation similar to FIG. 1a, showing the main branch of the bifurcation as having been tapered to minimize and/or substantially eliminate flow separation.

According to one embodiment of the present invention, delivering the stent to the deployment location comprises delivering the stent to a bifurcation site of the lumen, such as the bifurcation site shown in FIG. 1a, the bifurcation site having a main branch M and a side branch S and further corresponding to the deployment location of the stent. Additionally, expanding the stent comprises expanding the stent at the bifurcation site such that: in an expanded state thereof, an envelope 20 of the stent is asymmetrical with respect to a longitudinal axis thereof and defines a first portion, such as first portion 26 of FIGS. 6a-6b and 10 bounded by walls W1 and having a contour in a cross-sectional plane including the longitudinal axis of the stent that is either a curved line or a straight line angled with respect to the longitudinal axis. A contour of first portion 26 of the embodiment of FIGS. 6a-6b in the cross-sectional plane including the longitudinal axis of the stent 400 is provided for example in FIG. 6b, where the contour of wall W1 in that cross-sectional plane is curved line 30. A contour of first portion 26 of the embodiment of FIG. 10 in the cross-sectional plane including the longitudinal axis of stent 700 is provided for example in FIG. 10, where the contour of wall W1 is a straight line 30 angled with respect to the longitudinal axis.

Expanding the stent 400 or stent 700 according to embodiments of the present invention further comprises expanding the stent at the bifurcation site such that the stent envelope 20 further includes a second portion such as second portion 28 bounded by walls W2 of the embodiments of FIGS. 6a-6b and 10 bounded by walls W2 and having a contour in a cross-sectional plane including the longitudinal axis of the stent that is a straight line parallel to the longitudinal axis of the stent. This latter contour 32 is also shown in FIGS. 6b and 10. The first portion and the second portion together define the stent envelope 20 as shown after expansion of the stent 400 of FIGS. 6a-6b or stent 700 of FIG. 10 at the deployment site. According to an embodiment of the method for deploying of the present invention, the side W1 containing first portion 26 of the expanded stent with the taper is disposed opposite the side branch of the bifurcation site, while the side W2 with the second portion 28 without a taper abuts the side branch, that is, it is disposed adjacent to the side branch.

With respect to the delivery of an axially asymmetrical stent, such as, for example, that shown in the embodiments of FIGS. 6a-6b and 10, one could use a balloon with a preferential shape, or a delivery system such as those conventionally used in connection with bifurcation stents that give the operator control with respect to a rotational orientation of the stent relative to the anatomy.

The present invention further provides a stent that comprises a stent envelope adapted to be deployed at a deployment location in a lumen; and means associated with the stent envelope for controlling a flow of blood in the lumen when the stent envelope is in its expanded state so as to induce a favorable flow regime at the deployment location of the stent envelope relative a flow regime that would have been generated had a straight stent envelope been deployed at the deployment location for reducing a risk of restenosis at the deployment location. An example of such means has been provided with respect to embodiments of the present invention depicted in FIGS. 2a-10. Other means would be within the knowledge of a person skilled in the art.

It is to be understood, however, that stents of the present invention may be configured to have any of the various known cell and/or stent configurations, and may be made of any of the known materials for forming stents, as would be readily recognized by one skilled in the art. Any of the known materials, patterns and configurations of the stent walls known for making stents would benefit from the configuration of the stent envelope according to embodiments of the present invention. As was discussed in detail above, the stents may be self-expanding stents, balloon expandable stents or combinations of the two.

A stent according to the present invention may be made by any of the known methods of making stents, such as by a folding and welding method as described in U.S. Pat. Nos. 5,836,964, 5,922,005, 6,156,052, 5,997,703, 6,197,048 B1, and 6,114,049, or by laser cutting.

In addition, it is noted that the wire frame views in FIGS. 7a, 2b, 3b, 4b, 5b, 6b, 7b and 2c, 3c, 4c, and 5c, and 10 are not meant to be interpreted as showing cell patterns, stent patterns, or patterns of the actual walls of the stent itself, but rather as showing contours of the stent envelope as shown by theoretical lines that trace certain ones of those contours.

It is noted that the present invention permits physicians to use existing stents that were not originally designed to be tapered to carry out the present invention and to create a tapered geometry in a lumen as described above. The taper in the stent can be positioned at any desired treatment area in a lumen.

Although the present invention has been described using the example of "tapered" stents and balloons, it should be understood that configurations besides a taper are possible. Any configuration or shape which is designed to alter the characteristics of a lumen to induce a favorable flow regime that reduces a risk of restenosis is within the scope of the present invention. The important aspect is to tailor the stent to produce the desired geometry after implantation.

It should be noted that it is possible that there are other mechanisms of action which effect the lumen wall other than the ones described above with respect to blood cells of the white lineage. While we have proposed one mechanism of action, the present application is not bound to only this mechanism of action. Rather, the present application encompasses any shaped stent and method for creating a shaped stent, which is designed to minimize flow disturbances.

Moreover, while exemplary embodiments of a stent profile according to the present invention have been described above with respect to stent segments defined between respective boundary planes, the present invention includes within its scope the provision of stent configurations where transition regions between respective segments of the stent are not necessarily defined in planes, but are, for example, defined in a three-dimensional region.

Furthermore, although FIGS. 6a-6b and 10 were described as showing an axially asymmetric stent which may be used in a bifurcated lumen, it should be understood that any of the embodiments of the symmetric stent of the present invention, such as those shown in FIGS. 2a-5b, 7a and 7b, can also be used in a bifurcation geometry, and that any of the embodiments of an asymmetric stent of the present invention, such as that shown in FIGS. 6a-6b and 10, can also be used in a non-bifurcated geometry.

The invention has been described with reference to specific exemplary embodiments thereof. It will, however, be evident to persons having the benefit of this disclosure, that various modifications and changes may be made to these embodiments without departing from the broader spirit and scope of the invention. The specification and drawings are, accordingly, to be regarded in an illustrative rather than in a restrictive sense.

What is claimed is:

1. A stent for inducing a favorable flow regime in a lumen of a blood vessel, the stent having an envelope and a longitudinal axis along a direction of blood flow, whereby said envelope of said stent comprises a non-uniform asymmetrical shape about said longitudinal axis of the stent upon expansion, wherein said stent further comprises:
   a first stent segment having a first stent segment cross-sectional area in an expanded state of the stent;
   a second stent segment longitudinally offset with respect to the first stent segment and having a second stent segment cross-sectional area in an expanded state of the stent; and
   a third stent segment having a length, a circumference, a first end, and a second end, the first end of the third stent segment directly connected to the first stent segment at a plurality of points around the circumference of the third stent segment and the second end of the third stent segment directly connected to the second stent segment at a plurality of points around the circumference of the third stent segment,
   wherein the third stent segment defines a first part having said length and a second part having said length, each part defining a portion of the circumference of the third stent segment, the first part having a contour defining a constant angle with respect to said longitudinal axis along the entire length of the third stent segment, and the second part wherein said length of the third stent segment is parallel to said longitudinal axis of the stent.

2. The stent of claim 1, wherein the second part is quonset shaped.

3. The stent of claim 1, wherein said stent is a self-expanding stent.

4. The stent of claim 1, wherein said first stent segment cross sectional area and said second stent segment cross sectional area are different.

5. The stent of claim 1, wherein said stent is a balloon expandable stent and configured to be expanded on a delivery balloon to an asymmetrical shape.

6. The stent of claim 1 wherein said stent is a self-expanding stent having a symmetrical shape when delivered and initially expanded, and is configured to be expanded further on a balloon to an asymmetrical shape.

7. The stent of claim 1, wherein, in an expanded state of the stent:
   the first stent segment comprises a first right cylinder; and
   the second stent segment comprises a second right cylinder.

8. A delivery balloon for deploying the stent of claim 1, the balloon being configured to expand the envelope of said stent to an asymmetrical shape with respect to the longitudinal axis of the stent.

9. The balloon of claim 8, wherein the balloon includes:
   a first balloon segment configured to have a first balloon segment cross-sectional area in an inflated state of the balloon for expanding the first stent segment to the first stent segment cross-sectional area;
   a second balloon segment longitudinally offset with respect to the first balloon segment and configured to have a second balloon segment cross-sectional area in an inflated state of the balloon for expanding the second stent segment to the second stent segment cross-sectional area; and
   a third balloon segment having a length, a circumference, a first end, and a second end, the third balloon segment configured to assume a tapered balloon segment configuration in an inflated state of the balloon, the first end of the third balloon segment directly connected to the first balloon segment at a plurality of points around the circumference of the third balloon segment and the second end of the third balloon segment directly connected to the second balloon segment at a plurality of points around the circumference of the third balloon segment.

10. The balloon of claim 9, wherein the second balloon segment cross-sectional area is different from the first balloon segment cross-sectional area.

11. A kit for deploying a stent comprising the stent of claim 1, the kit further including a delivery balloon configured to be inflated for expanded the stent in a lumen such that the envelope of said stent has an asymmetrical shape upon expansion with respect to the longitudinal axis of the stent.

12. The kit of claim 11, wherein the balloon includes:
a first balloon segment configured to have a first balloon segment cross-sectional area in an inflated state of the balloon for expanding the first stent segment to the first stent segment cross-sectional area;
a second balloon segment longitudinally offset with respect to the first balloon segment and configured to have a second balloon segment cross-sectional area in an inflated state of the balloon for expanding the second stent segment to the second stent segment; and
a third balloon segment having a length, a circumference, a first end, and a second end, the third balloon segment configured to assume a tapered balloon segment configuration in an inflated state of the balloon, the first end of the third balloon segment directly connected to the first balloon segment at a plurality of points around the circumference of the third balloon segment and the second end of the third balloon segment directly connected to the second balloon segment at a plurality of points around the circumference of the third balloon segment.

13. The kit of claim 12, wherein the second balloon segment cross-sectional area is different from the first balloon segment cross-sectional area.

14. The stent of claim 1, wherein the contour of the first part is a decreasing taper in the direction of blood flow.

15. The stent of claim 1, wherein the contour of the first part comprises a straight line at an angle with respect to the longitudinal axis of the stent.

* * * * *